(12) United States Patent
Yiu

(10) Patent No.: US 9,449,123 B2
(45) Date of Patent: Sep. 20, 2016

(54) STRESSES INDUCED BY RANDOM LOADING

(75) Inventor: Hoi Yiu, Bristol (GB)

(73) Assignee: Airbus Operations Limited, Bristol (GB)

(*) Notice: Subject to any disclaimer, the term of this patent is extended or adjusted under 35 U.S.C. 154(b) by 586 days.

(21) Appl. No.: 13/414,823

(22) Filed: Mar. 8, 2012

(65) Prior Publication Data

US 2012/0239358 A1 Sep. 20, 2012

(30) Foreign Application Priority Data

Mar. 16, 2011 (GB) .................................. 1104413.8

(51) Int. Cl.
   *G06F 17/50* (2006.01)
   *G06G 7/48* (2006.01)
(52) U.S. Cl.
   CPC .................................. *G06F 17/5018* (2013.01)
(58) Field of Classification Search
   None
   See application file for complete search history.

(56) References Cited

U.S. PATENT DOCUMENTS

| 6,363,789 | B1* | 4/2002 | Rassaian et al. | 73/663 |
| 6,704,664 | B2* | 3/2004 | Su et al. | 702/34 |
| 6,813,749 | B2* | 11/2004 | Rassaian | 703/7 |
| 2003/0016832 | A1* | 1/2003 | Naganarayana | G06F 17/5018 381/71.4 |
| 2003/0114995 | A1* | 6/2003 | Su | G06F 17/5018 702/34 |

OTHER PUBLICATIONS

Search Report for GB 1104413.8 dated Jul. 13, 2011.
Caillaud et al., "Correction factors for ASME ANSI-OM3 Stress/Velocity Relationship With Respect to Static Design", *Int'l. Conf. on Structural Mechanics in Reactor Technology*, Aug. 2003, pp. 1-8.
Reese et al., "A Tutorial on Design Analysis for Random Vibration", *Sandia National Laboratories*, 2000, 19 pages.
Blevins, "An Approximate Method for Sonic Fatigue Analysis of Plates and Shells", *Journal of Sound and Vibration*, vol. 129(1), 1989, pp. 51-71.
Hampton, "MSC/NASTRAN Stress Analysis of Complete Models Subjected to Random and Quasi-Static Loads", *NASA/TM-2000-209585*, 2000, 36 pgs.

\* cited by examiner

*Primary Examiner* — Omar Fernandez Rivas
*Assistant Examiner* — Nithya J Moll
(74) *Attorney, Agent, or Firm* — Nixon & Vanderhye P.C.

(57) ABSTRACT

A computer-implemented method of modelling a root-mean-square stress in a structure induced by a random load. The method comprises determining a modal correction factor based on data representing the eigensolution for the structure in free vibration. The modal correction factor characterizes the proportion of the random load, which is attributable to the root-mean-square response of the structure. Once the modal correction factor has been calculated, it is applied to data representing a stress in the structure due to a forced vibration to thereby determine the root-mean-square stress induced by the random load.

19 Claims, 5 Drawing Sheets

STRESSES INDUCED BY RANDOM LOADING

This application is claims priority to GB Patent Application No. 1104413.8 filed 16 Mar. 2011, the entire contents of which is hereby incorporated by reference.

FIELD OF INVENTION

The present invention relates to a computer-implemented method of modelling a stress in a structure induced by a random load.

BACKGROUND OF THE INVENTION

A random vibration is a motion which is non-deterministic and which cannot be accurately predicted in a deterministic manner. Instead, a random vibration can be characterised statistically (e.g. based on historic data) and statistical techniques can be used to predict the motion of the random vibration (e.g. the probability of a particular acceleration and displacement magnitude in a particular time-period). A random vibration in a structure is typically induced by a random load (e.g. an acoustic pressure load or a mass subjected to inertia effects under random oscillation). The response of a structure subject to a random load is generally characterised in terms of root-mean-square quantities (such as stress or displacement), which provide a mean value of the particular random quantity over time.

A random load typically comprises all frequencies within a given frequency range at all times. Accordingly, when a random load is applied to a structure, all resonance modes of the structure within the frequency range of the random load will be excited at the same time and random vibration will result. Consequently, a fatigue analysis of a structure under random vibration is different to a fatigue analysis of the structure under harmonic excitation.

The stress induced in a structure due to random vibration is a useful parameter for assessing the strength and fatigue endurance of the structure. Assessments of this kind are important in a number of industries, including the aviation and automotive industries. For example, fatigue in airframe structures due to acoustic loading is a particular safety concern in the aviation industry, and airworthiness authorities typically require that airframe structures meet prescribed minimum standards, as determined by computational analysis, experimental testing and aircraft service history.

In order to address the above requirements, there has been much effort to develop methods that can accurately predict the stresses in structures induced by random vibration. However, current methods remain either prohibitively expensive (in a computational sense) or incapable of providing the required accuracy. Thus, additional experimental evidence is normally required before the structure in question can be deployed in an operational environment.

For simple structures, a forced response analysis is a practical analysis tool for determining the stress in a structure due to random vibration. However, the direct solution (or closed-form solution) for a forced response analysis is confined to simple cases such as single-degree-of-freedom structures. In reality, most structures behave as multiple-degrees-of-freedom systems.

More recently, numerical methods such as the Finite Element Method (FEM) have been used to model the stresses in structures induced by random loading. FEM is a numerical technique for finding approximate solutions to partial differential equations (PDEs). The method involves discretisation of the structure (or "domain") into a plurality of elements (the "mesh") defined by points in space ("nodes"). For each element in the domain, the relevant PDEs to be solved can be approximated using linear functions. The result of the discretisation process for all elements in the domain is a large dimensional linear problem of finite dimension, the solution of which will approximately solve the original PDEs. A skilled person would be well versed in implementation of FEM and its use, and further details will not be discussed herein.

With the advent of increased computing speeds, software codes employing FEM, such as NASTRAN™ (as implemented in MSC NASTRAN™ by MSC Software Corporation, Santa Ana, Calif., USA) have been used to perform direct random response analyses of complex structures subjected to a random loading. However, such analyses involve direct solution of the equations of motion for the structure in question over the range of frequencies defining the random loading. Such analyses are complex and the required computational power is often prohibitive, thereby limiting their application to simple structures comprising relatively few degrees of freedom.

Blevins [1] demonstrated a method for calculating the response of a structure due to forced vibration, based on a normal modal solution obtained from finite element analysis. Blevins demonstrated that an N by N multiple-degrees-of-freedom system could be transformed to N single-degree-of-freedom systems; each single-degree-of-freedom system being solvable using a direct (or closed-form) solution.

Conventionally, the deflection of a single-degree-of-freedom system can be solved in exact form by applying a force (either harmonic or random oscillating) to a mass, spring and damping system. In such systems, the deflection is proportional to stress, which itself is dependent on the applied boundary conditions (e.g. clamped or supported edges). The maximum stress can be calculated by scaling the maximum deflection obtained from the modal solution for the structure. For this purpose, Blevins defined a scaling factor termed the "characteristic pressure", which is a function of the applied loading and the Maximum deflection obtained from the modal solution. The maximum stress can then be calculated using the characteristic pressure and the relation of deflection to stress.

After the stress in a single degree-of-freedom system is derived, a correction to the multi-degrees-of freedom system is required. To this end, Blevins developed a modal correction factor (termed a joint acceptance factor), which characterises the proportion of the random loading that can excite each particular structural mode in the structure. Blevins studied a number of different analytical cases and proposed a modal correction factor of 1.621 for the first mode in the case of a simply supported plate structure.

One drawback of the method proposed by Blevins is that it requires an analytical form of the modal correction factor. Analytical forms for the modal correction factor are only available for a limited range of simple structures (e.g. flat panels). Thus, it will be apparent that the Blevins method can only be applied to a limited range of structures, and cannot be used to model complex structures for use in practical applications.

In view of the impracticalities discussed above, it will be apparent that improved modelling methods are required for practical modelling of the stresses arising in complex structures due to random vibration. Embodiments of the present invention seek to address this need.

SUMMARY OF THE INVENTION

In accordance with one aspect of the invention, there is provided a computer-implemented method of modelling a root-mean-square stress in a structure induced by a random load, the method comprising: determining a modal correction factor based on data representing the eigensolution for the structure in free vibration, the modal correction factor characterising the proportion of the random load which is attributable to the root-mean-square response of the structure; and applying the modal correction factor to data representing a stress in the structure due to a forced vibration to thereby determine the root-mean-square stress induced by the random load.

In some embodiments, the method further comprises determining the eigensolution using a finite element method modal analysis.

In some embodiments of the method, the random load is characterised by a power spectral density.

In a further embodiment of the method, for a particular location in the structure, the stress due to the forced vibration is determined as being proportional to a corresponding modal stress in free vibration. Moreover, in some embodiments, for a particular location in the structure, the ratio of the stress in the structure due to the forced vibration and the corresponding modal stress in free vibration is determined using the Miles equation:

$$\frac{\sigma_i(x, y, z)_{rms}}{\overline{\sigma}_i(x, y, z)} = \sqrt{\frac{\pi \omega_i}{4 \zeta_i} \frac{G(\omega_i)}{\overline{P}_i^2}},$$

where $\sigma_i(x,y,z)_{rms}$ is the stress at a position x, y, z in the structure due to the forced vibration; $\overline{\sigma}_i(x,y,z)$ is the modal stress at a position x, y, z in due to free vibration in mode i; $\omega_i$ is the frequency of mode i; $\zeta_i$ is the critical damping for mode i; $G(\omega_i)$ is the power spectral density characterising the random load; and $\overline{P}_i$ is a characteristic pressure for mode i.

In a preferred embodiment of the method, the modal correction factor is calculated as:

$$J_i = \frac{[\phi]_i^T \begin{Bmatrix} 1 \\ \vdots \\ 1 \end{Bmatrix}}{[\phi]_i^T [\phi]_i},$$

where: $J_i$ is the modal correction factor for the $i^{th}$ mode; and $[\phi]_i$ is the eigenvector solution for mode i.

In some embodiments, the method further comprises displaying, using a visual display device, the root-mean-square stresses determined for a plurality of locations in the structure for inspection by a user.

In some embodiments, the random load is an acoustic pressure. Moreover, the acoustic pressure can be characterised as:

$$p_{rms} = 10^{\left[\frac{L_{ps}}{20} - 4.69897\right]},$$

where $p_{rms}$ is the root-mean-square pressure and $L_{ps}$ is the sound pressure spectrum level.

In accordance with a further aspect of the invention, there is provided a computer program product comprising a non-transitory computer-readable storage medium having computer readable instructions stored thereon, the computer readable instructions being executable by a computerised device to cause the computerised device to perform a method of modelling a root-mean-square stress in a structure induced by a random load, the method comprising: determining a modal correction factor based on data representing the eigensolution for the structure in free vibration, the modal correction factor characterising the proportion of the random load which is attributable to the root-mean-square response of the structure; and applying the modal correction factor to data representing a stress in the structure due to a forced vibration to thereby determine the root-mean-square stress induced by the random load.

In accordance with a yet further aspect of the invention, there is provided a computer apparatus for modelling a root-mean-square stress in a structure induced by a random load, the apparatus comprising a processor configured to: determine a modal correction factor based on data representing the eigensolution for the structure in free vibration, the modal correction factor characterising the proportion of the random load which is attributable to the root-mean-square response of the structure; and apply the modal correction factor to data representing a stress in the structure due to a forced vibration to thereby determine the root-mean-square stress induced by the random load.

BRIEF DESCRIPTION OF THE DRAWINGS

Further features and advantages of the invention will become apparent from the following description of embodiments of the invention, given by way of example only, which is made with reference to the accompanying drawings, of which.

Several steps, parts and components of the described embodiments appear in more than one Figure; for the sake of clarity, the same reference numeral will be used to refer to the same step, part and component in all of the Figures.

DETAILED DESCRIPTION OF EMBODIMENTS OF THE INVENTION

Figure 1A:
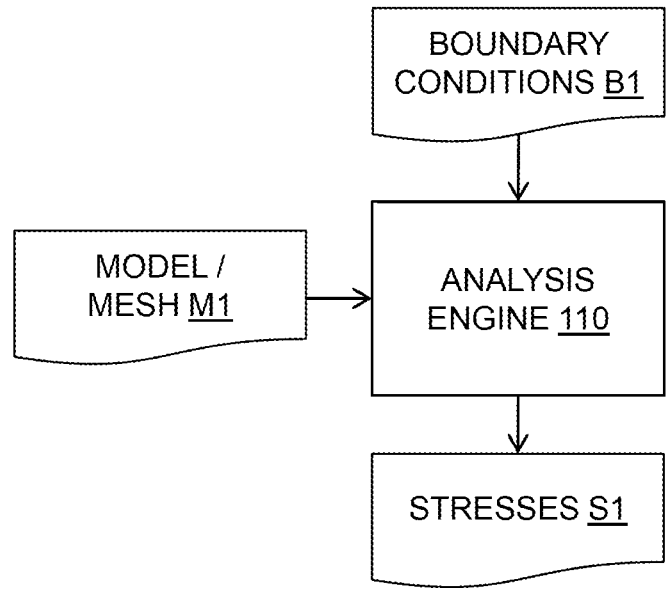
FIG. 1A is a schematic block diagram of an analysis engine in accordance with an embodiment of the invention.

FIG. 1A shows an analysis engine 110 for modelling the stresses induced in a structure due to a random loading, in accordance with a first embodiment of the invention. The analysis engine 110 receives data M1 representative of a CAD (Computer Aided Design Model) model or mesh of the structure to be analysed. The CAD model may be generated using any suitable CAD software (e.g. SolidWorks™ or CATIA™ of Dassault Systems of France). The analysis engine 110 also receives data B1 representative of the boundary conditions and the random loading to be applied to the structure. The analysis engine 110 is configured to receive data M1 and data B1 and perform an analysis to determine one or more stresses induced by the random loading, represented by data S1.

Figure 1B:
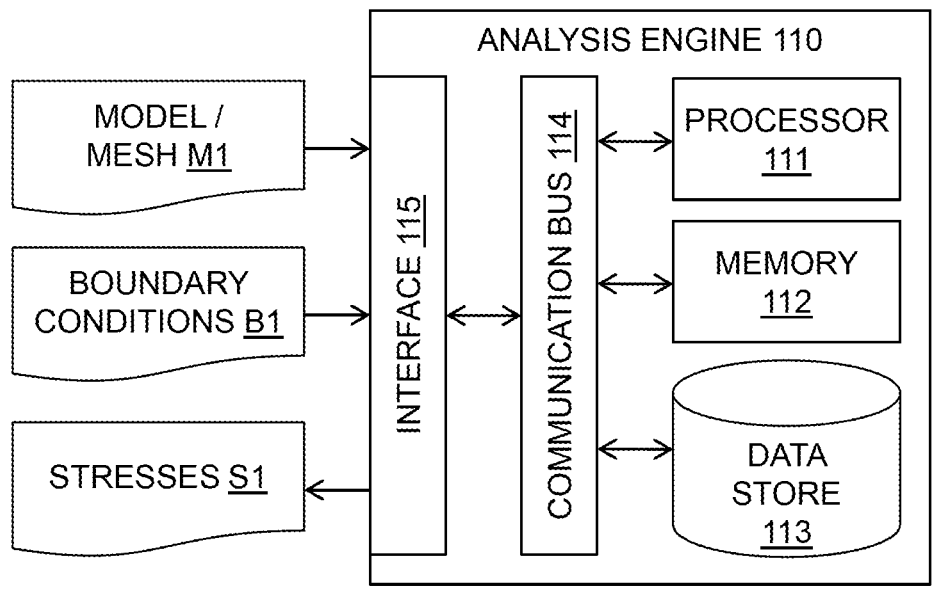
FIG. 1B is a schematic block diagram of an analysis engine in accordance with a further embodiment of the invention.

With reference to FIG. 1B the analysis engine 110 typically comprises a processor 111, a memory 112, a data store 113, a communications bus 114 and an interface 115. The communications bus 114 provides a means for transferring data between the processor 111, memory 112, data store 113 and interface 115. Memory 112 may be volatile memory such as RAM or non-volatile memory such as EPROM or flash memory. The data store 113 is typically a magnetic, solid state (e.g. flash memory) or optical storage medium arranged for storing data such as a database, a table, or a plurality of files. The processor 111 will typically be a software-controlled microprocessor (for example an Intel Pentium™ processor) or an application specific integrated circuit (ASIC) or the like. The interface 115 provides means for transmitting and receiving data, such as data M1, B1 and S1. The processor 111 is configured to interact with the memory 112, data store 113 and interface 115 to perform a number of functions according to a software program, as will be described below. However, it will be appreciated that functionality may equally be realised using firmware, or an appropriate combination of both software and firmware. Optionally, the analysis engine 110 may additionally comprise a visual display unit such that data may be displayed graphically for visual inspection (not shown).

Figure 1C:
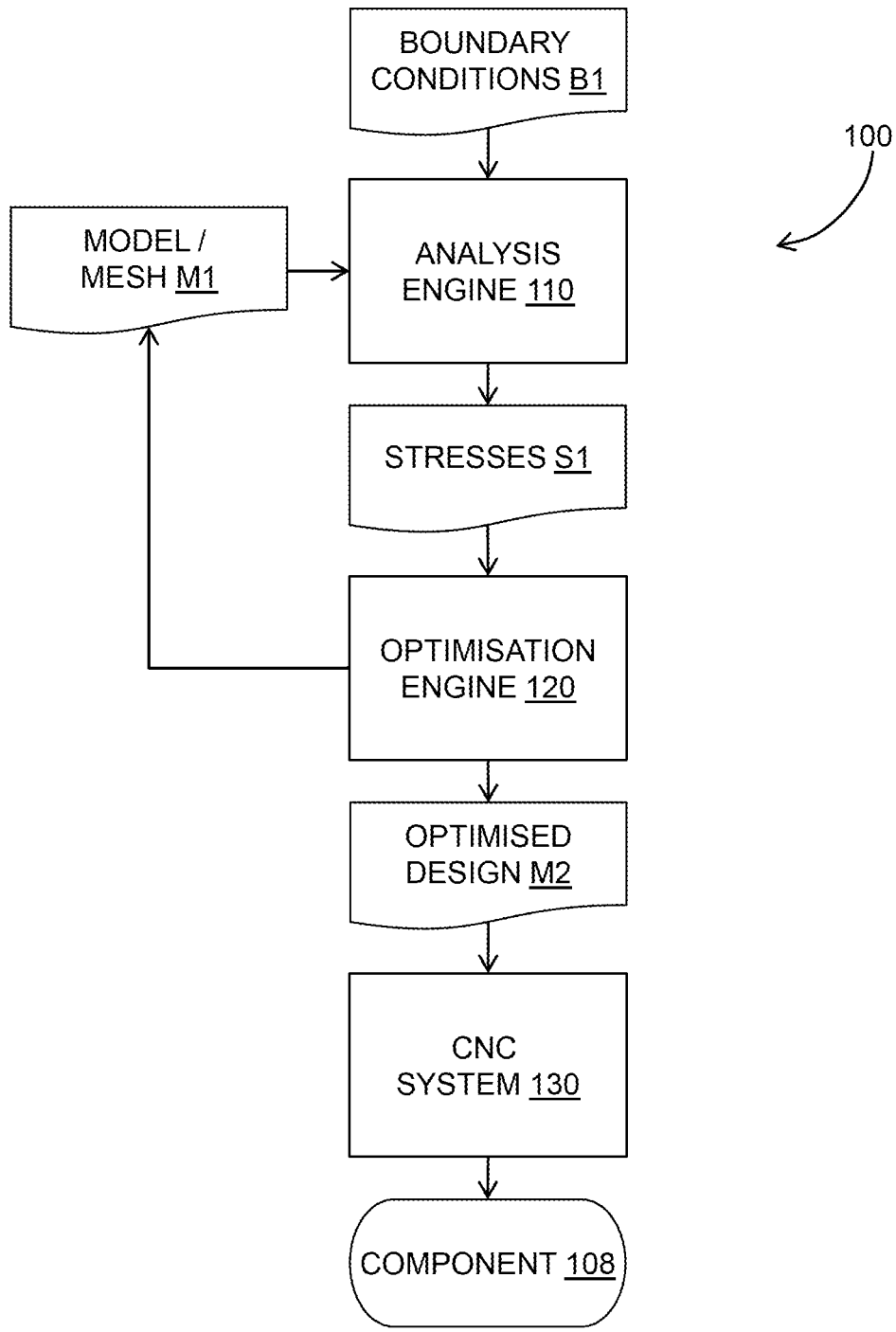
FIG. 1C is a schematic block diagram of an optimisation system in accordance with a yet further embodiment of the invention.

FIG. 1C shows a system 100 for optimising and manufacturing components for use in applications involving random loading, in accordance with a further embodiment of the invention. The system includes the analysis engine 110 of FIGS. 1A and 1B, an optimisation engine 120, and a computer numerically controlled (CNC) manufacturing system 130. The analysis engine 110 receives data M1 in the form of a CAD model representing an initial component design. Typically, the CAD model M1 is parameterised based one or more dimensional relationships, and includes one or more physical constraints (e.g. maximum or minimum dimensions, maximum weight etc). The analysis engine 110 further receives data B1, which is representative of the boundary conditions and the random loading to be applied to the structure. Upon receipt of data M1 and B1, the analysis engine performs an analysis to determine one or more stresses in the component due to the random loading. The results of the analysis are sent to optimisation engine 120 which may in turn adjust one or more parameters in the CAD model and return the model to the analysis engine 110 for further analysis. For example, the optimisation engine may be configured to minimise the maximum stress arising in the component structure (within the constraints defined in M1). In this way, the analysis engine 110 and the optimisation engine 120 cooperate iteratively to produce an optimised component design within the initial constraints defined in the CAD model represented by M1. Optionally, the optimised model, represented by data M2, is passed to the CNC system 130, which proceeds to manufacture a component 108 according to the optimised design M2.

The analysis engine 110 shown in FIGS. 1A, 1B and 1C employs FEM and a modified Blevins method to model the stresses in the structure induced by the random load. An explanation of the modified Blevins method is provided below.

The general Finite Element formulation of the equation of motion in discretised form for dynamic analysis of the structure to be analysed takes the following matrix form $$[M]\{\ddot{u}\}+[C]\{\dot{u}\}+[K]\{u\}=\{P\}, \quad (1)$$

where $[M]$, $[C]$ and $[K]$ are the mass, damping and stiffness coefficient matrices respectively (resulting from the discretisation over the structure domain). The mass coefficient matrix $[M]$ can be either consistent mass or lumped mass [2]. The force vector $\{P\}$ represents the load applied to the structure at each node in the domain.

Free vibration (i.e. no application of an external force) of the structure in the absence of damping is given by the solution of the matrix equation $$[M]\{\ddot{u}\}+[K]\{u\}=\{0\}, \quad (2)$$

and applying a frequency transformation to Equation 2 (i.e. $\{u\}=\{\phi\}e^{i\omega t}$ and $\{P\}=\{p\}e^{i\omega t}$ where w is the frequency of vibration) produces $$\lfloor K-\omega^2 M\rfloor\{\phi\}=\{0\}, \quad (3)$$

which is a linear eigenvalue problem, the solution (the "eigensolution") of which corresponds to one or more modes of free vibration in the structure. More specifically, the eigensolution comprises a plurality of eigenvalues and corresponding eigenvectors; each eigenvalue representing the square of a natural frequency of the structure, and each corresponding eigenvector representing the shape of the mode of vibration. An FEM analysis of this type is known as a "modal analysis" and the determined natural frequencies are known as the "normal modes".

The random loading, which is applied to the structure, can be represented by a random Power Spectral Density (PSD) function. As discussed above, the random loading may, for example, relate to an acoustic pressure or forcing due to inertial effects. In the FEM, a random loading can typically be resolved to a force, which is applied at one or more nodes in the mesh representing the structure.

Where the random loading is an acoustic pressure, the associated pressure spectrum level or the root mean square (RMS) pressure, $p_{rms}$, can be given by the following expression [3]

$$p_{rms}=10^{\left[\frac{L_{ps}}{20}-4.69897\right]}, \quad (4)$$

where $L_{ps}$ is the sound pressure spectrum level (for example, bandwidth conversions and explanations can be found in ESDU 66017 [3]). The power spectral density per Hertz, $G(\omega)$, is mathematically the square of the RMS pressure, $p_{rms}$, and it is frequency dependent as shown below:

$$G(\omega)=[p_{rms}]^2. \quad (5)$$

The RMS stresses induced by the random loading applied to the structure can be derived from the Miles equation [1,4]. The Blevins method reduces a system with N by N degrees-of-freedom to a set of N single degree of freedom equations. Thus, the RMS stress, $\sigma_{i,rms}$ and deformation, $w_{i,rms}$, due to a forced vibration in a particular mode, i, can be linearly related to the modal stress, $\bar{\sigma}_i$, and deformation, $\phi_i$, determined from a modal analysis for the respective mode (note: overbar represents a modal quantity). When the applied random loading has a random broadband spectrum, then from Miles equation [4] one obtains $$\frac{w_i(x, y, z, t)_{rms}}{\phi_i(x, y, z)} = \frac{\sigma_i(x, y, z, t)_{rms}}{\overline{\sigma}_i(x, y, z)} = \sqrt{\frac{\pi f_i}{4\zeta_i} \frac{G(\omega_i)}{\overline{P}_i^2}}, \quad (6)$$

where $\omega_i$ is the frequency of mode i and $\overline{P}_i$ is the characteristic modal pressure for mode i. In the case of a plate structure, the modal pressure is calculated as:

$$\overline{P}_i = \rho h (2\pi\omega_i)^2 |\phi_i(x,y,z)|_{max}, \quad (7)$$

where $|\phi_i(x,y,z)|_{max}$ is the maximum modal displacement for mode i and h is the thickness of the plate.

Generally, it is reasonable to approximate both the structural and the loading waveforms as sinusoidal. However, with a random loading, there is potential for more than one structural mode to be excited by a particular frequency. Thus, to account for these effects, a modal correction factor (otherwise termed a joint acceptance factor) is required.

The modal correction factor characterises the proportion of the applied random loading that the particular structural mode can accept, thus determining the response of the structure in question. Since there is not a perfect match between the acoustic wavelength and the structural mode, the correction factor for a particular node is not necessarily equal to 1. Rearranging Equation 6 and applying the modal correction factor, $J_i$, results in the following expression for the resultant RMS stresses, $\sigma_i(x,y,z)_{rms}$, at position x, y, z due to the random vibration of the structure.

$$\sigma_i(x, y, z)_{rms} = J_i \times \overline{\sigma}_i(x, y, z) \sqrt{\frac{\pi \omega_i}{4\zeta_i} \frac{G_s(\omega_i)}{\overline{P}_i^2}}. \quad (8)$$

For a flat panel with sinusoidal deformation, Blevins provided an analytical value of the modal correction factor of $J_{2D} = 1.27^2 = 1.62$ for the first structural mode with all edges simply supported. However, as discussed above, analytical forms for the modal correction factor are only available for a limited range of simple structures (e.g. flat panels). Thus, it will be apparent that the Blevins method can only be applied to a limited range of structures, and cannot be used for complex structures.

Accordingly, embodiments of the invention provide a method for modelling stresses in a structure due to random loading, which is applicable to structures with arbitrary geometry. Thus, embodiments of the invention find application as a generic analysis tool for complex structures where an analytical form of the modal correction factor is not known or available.

Matrices [M] and [K] of Equations 1 and 2 are sparsely populated and symmetrical. For free vibration, the undamped natural modes and natural frequencies can be determined from eigenvalue solution to Equation 2. If the mass-normalised mode shape is $[\phi]$ from the eigenvalue solution, Equation 1 can be transformed to a set of generalized coordinates $\{q\}$ using the eigenvectors (or mode shapes) because of the orthogonal characteristics of the eigenvectors:

$$\{u\} = [\phi]\{q\}, \{\dot{u}\} = [\phi]\{\dot{q}\}, \{\ddot{u}\} = [\phi]\{\ddot{q}\} \quad (9)$$

Substituting these into the equation of motion for the structure (Equation 1) gives $$[M][\phi]\{\ddot{q}\} + [C][\phi]\{\dot{q}\} + [K][\phi]\{q\} = \{P\}, \quad (10)$$

and pre-multiplication by the transpose of the mass-normalized mode shape $[\phi]^T$ gives $$[\phi]^T[M][\phi]\{\ddot{q}\} + [\phi]^T[C][\phi]\{\dot{q}\} + [\phi]^T[K][\phi]\{q\} = [\phi]^T\{P\}.$$

As discussed, above, the mass normalized eigenvectors, $[\phi]$, can be obtained from a FEM modal analysis (e.g. provided by the NASTRAN™ modal analysis using solver SOL 103).

As a result of the orthogonality of the eigenvectors, $[\phi]$, Equation 11 can be decoupled into a system of N by N individual equations $$[I]\{\ddot{q}\} + [c_i/m_i]\{\dot{q}\} + [k_i/m_i]\{q\} = [\phi]^T\{P\}, \quad (12)$$

where [I] is the unit matrix and $[c_i/m_i]$ and $[k_i/m_i]$ are diagonal matrices. Comparing Equation 12 and Equation 20 of [1], reveals that the transform method converts the structure into N uncoupled single-degree-of-freedom equations. Each of the single degree-of-freedom equation represents a dynamic modal stage of the structure. The term $k_i/m_i$ can be expressed by the natural modal frequency of the structure, $\omega_i^2$, and the damping can be expressed as $2\zeta\omega_i$. Further, the standard dynamic characteristic function for the Miles equation is $k - m\omega^2 + ic\omega$, which differs to Equation 12 by division by the modal mass. Alternatively, one can divide the right hand forcing term of Equation 12 by the modal mass. The modal mass can be calculated from mass normalised eigenvectors as $[m_i]^{-1} = [\phi]_i^T[\phi]_i$, where $[m_i]$ is a diagonal matrix.

For a particular mode, i, Equation 11 can be rewritten as $$m_i \ddot{q} + c_i \dot{q} + k_i q = \frac{[\phi]_i^T \{P\}}{[\phi]_i^T [\phi]_i}. \quad (13)$$

If a uniform pressure is applied to the surface of the structure, the pressure vector $\{p\}$ can be expressed as $$\{P\} = \overline{P}_{i,0} \begin{Bmatrix} 1 \\ \vdots \\ 1 \end{Bmatrix}, \quad (14)$$

where $\overline{P}_{i,0}$ is modal characteristic pressure, which will give the maximum deflection in mode i.

From Equation 13, the modal correction factor, $J_i$, converts the matrix equation to a single-degree-of-freedom equation. Inspection of Equation 13 reveals $$J_i = \frac{[\phi]_i^T \begin{Bmatrix} 1 \\ \vdots \\ 1 \end{Bmatrix}}{[\phi]_i^T [\phi]_i}. \quad (15)$$

It will be noted that the eigenvector, $[\phi]_i$, must be in the normal direction of the surface of the structure and normalised by the maximum value $[\phi]_i = [\phi]_i / \|\phi\|_{i,max}$. Each mode consists of the eigenvectors in x, y and z direction and another three eigenvectors in rotational degrees-of-freedom. Further, only the three linear eigenvectors in the x, y and z directions contribute to the modal correction factor. Thus, the modal correction factor can be calculated separately in each direction and $J_{i,x}$, $J_{i,y}$ and $J_{i,z}$, and the resultant joint acceptance function, $J_{i,r}$, can be calculated as $$J_{i,r}=\sqrt{J_{i,x}^2+J_{i,y}^2+J_{i,z}^2}. \quad (16)$$

To summarise, the eigenvalue solution, $[\phi]_i$, determined from the modal analysis of the structure is used to calculate the modal correction factor which is subsequently used to calculate the stresses resulting from the random loading.

Typically, the first structural mode is most significant when modelling the RMS stresses due to a random load. The higher structural modes can be calculated using embodiments of the invention; however, it is generally sufficient (though not essential) to estimate the root-mean-square structural response based the first structural mode only.

Figure 2A:
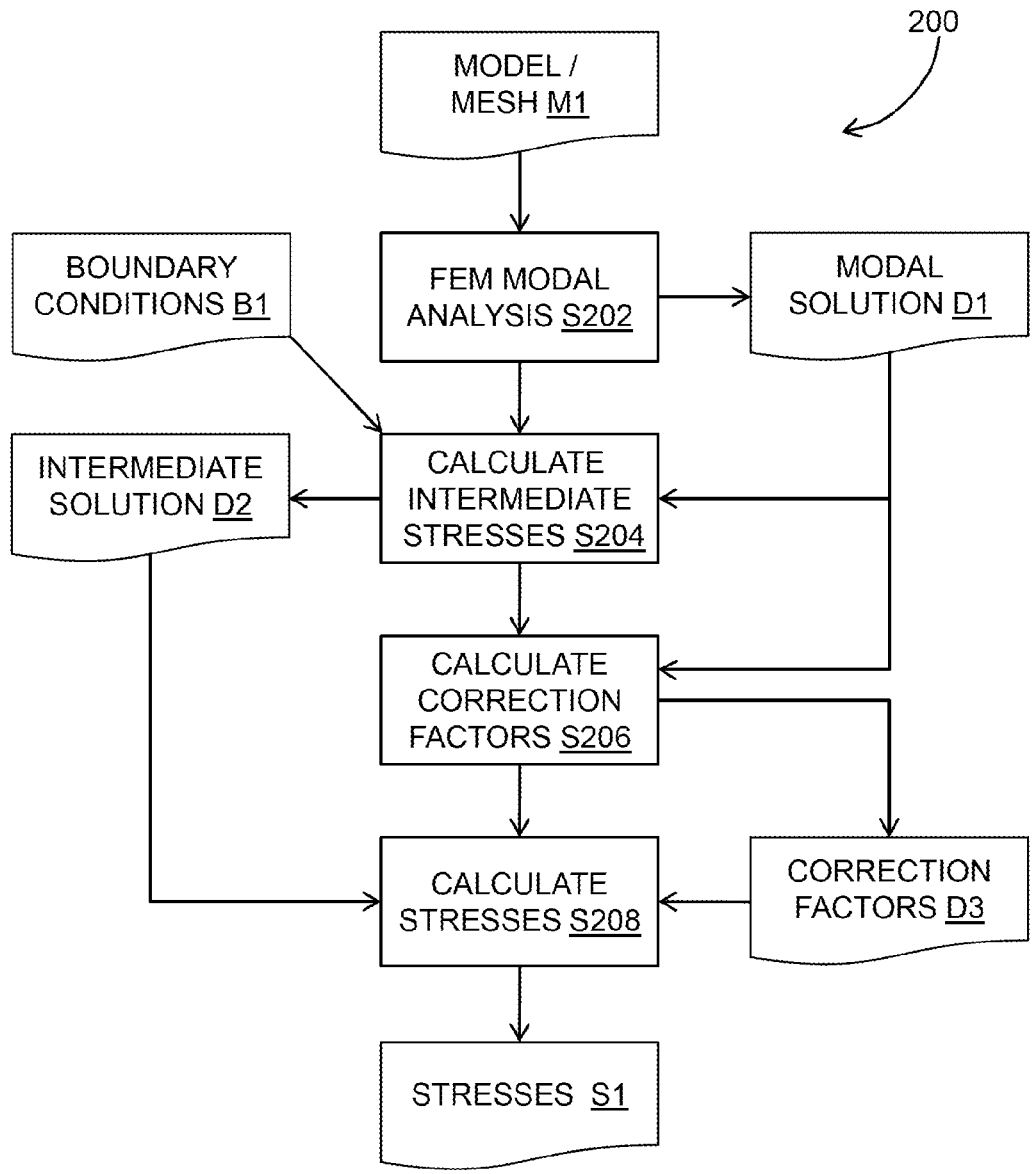
FIG. 2A is a flow chart illustrating a computer-implemented method in accordance with an embodiment of the invention.

As discussed above, embodiments of the analysis engine 110 employ a computer-implemented method based on the modified Blevins method. The steps involved in an embodiment of such a method 200 is shown in FIG. 2A and described below.

Step S202: Firstly, a FEM modal analysis is performed using FEM based on data M1 defining a mesh representative of the structure to be analysed. The modal analysis provides (i) the natural frequency $\omega_i$; (ii) the mode shape, $[\phi]_i$; and (iii) the modal stresses $\bar{\sigma}_i$ associated with the deformation in each mode i. The modal solution is output as data D1.

Step S204: Next, the uncorrected RMS stresses and deformations (hereinafter termed "intermediate" stresses and deformation) are determined based on the modal solution D1 and one or more boundary conditions defining the random loading B1. For example, in the case of an acoustic loading, data B1 will typically comprising data defining the sound pressure spectrum level, $L_{ps}$, for the acoustic pressure, which can be used to calculate the RMS acoustic pressure, $p_{rms}$ (using Equation 4), the power spectral density, $G(\omega)$ (using Equation 5), and the characteristic modal pressure, $\bar{P}_i$ (using Equation 7). Once these parameters have been calculated, the intermediate stresses and deformations in the structure are determined using Equation 6. In an alternative embodiment, the RMS acoustic pressure, $p_{rms}$, and the corresponding power spectral density, $G(\omega)$ may be pre-calculated and defined in data D3. The intermediate stresses and deformations calculated from Equation 6 are output as data D2.

Step S206: Next, the modal correction factors, $J_i$, are determined based on the modal solution D1 and Equations 15 and 16.

Step S208: The acoustic stresses and deformations are determined by applying the modal correction factors determined in step S206 to the intermediate stresses and deformations determined in S204 in accordance with Equation 8. The output of step S208 is typically a data file S1 comprising data representative of one or more stresses in the structure induced by the random loading. The data contained in file S1 may be used to identify those areas of the structure that may be more susceptible to acoustic fatigue than other areas (i.e. the RMS stresses exceed a threshold level, above which fatigue is known to occur). In some embodiments, the data contained in data file S1 may be represented graphically using a suitable post-processing software application, such as PATRAN™ of MSC Software Corporation, thus allowing a user to inspect visually the acoustic stresses in the structure.

Figure 2B:
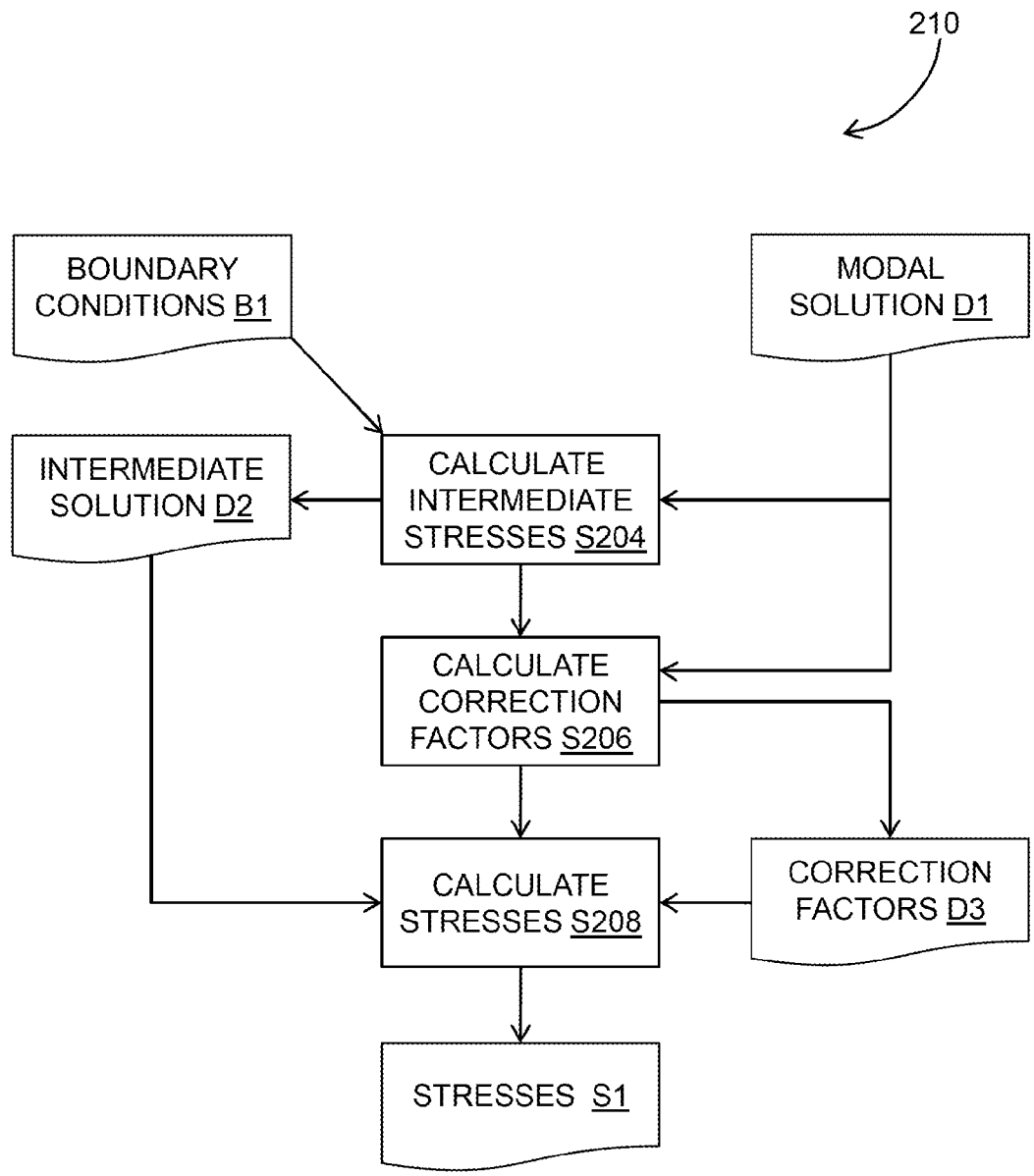
FIG. 2B is a flow chart illustrating a computer-implemented method in accordance with a further embodiment of the invention.

FIG. 2B shows a further embodiment of the invention implemented as a FEM post-processing method 210. Steps S204-S208 and data B1, S1 and D1-D3 of FIG. 2B correspond to steps S204-S208 and data B1, S1 and D1-D3 of FIG. 2A respectively. However, it will be apparent that the post-processing method 210 of FIG. 2B does not include the FEM modal analysis step S202 of FIG. 2A. Instead, modal solution is pre-computed and received as data D1 and steps S204-S208 represent post-processing of the modal solution. Thus, it will be apparent that embodiments of the invention may be implemented as a post-processing method for FEM software such as NASTRAN™.

The computer implemented methods shown in FIGS. 2A and 2B are described as a series of blocks representing steps in the method. However, it is to be appreciated that the methodologies are not limited by the order of the blocks, as some blocks can occur in different orders and/or concurrently with other blocks from that shown and described. For example, in some embodiments of the invention, the calculation of the correction factors at step S206 may be performed prior to calculation of the intermediate stresses and deformations at step S204. Moreover, it is to be appreciated that in some embodiments, the illustrated steps may be combined, or the functionality of a single block may be separated into separate and distinct steps.

It will be further appreciated that the methods of FIG. 2A and FIG. 2B can be implemented in software comprising a plurality of instructions that can be read, interpreted, compiled, and/or executed and that cause a computer, processor, or other electronic device to perform described functions. The instructions may be embodied in various forms like routines, algorithms, modules, methods, threads, and/or programs including separate applications or code from dynamically and/or statically linked libraries. Software may also be implemented in a variety of executable and/or loadable forms including, but not limited to, a stand-alone program, a function call (local and/or remote), a servelet, an applet, instructions stored in a memory, part of an operating system or other types of executable instructions. It will also be appreciated that computer-readable and/or executable instructions can be located in one logic and/or distributed between two or more communicating, co-operating, and/or parallel processing logics and thus can be loaded and/or executed in serial, parallel, massively parallel and other manners. Common forms of a computer-readable media include, but are not limited to, floppy disks, hard disks, magnetic tape, other magnetic media, CD-ROM, other optical media, RAM, ROM, EPROM, Flash and other media from which a computer, a processor or other electronic device can read.

Application of embodiments of the invention will now be described with reference to the following three examples.

Example 1

Flat Panel Subjected to Acoustic Pressure

Figure 3A:
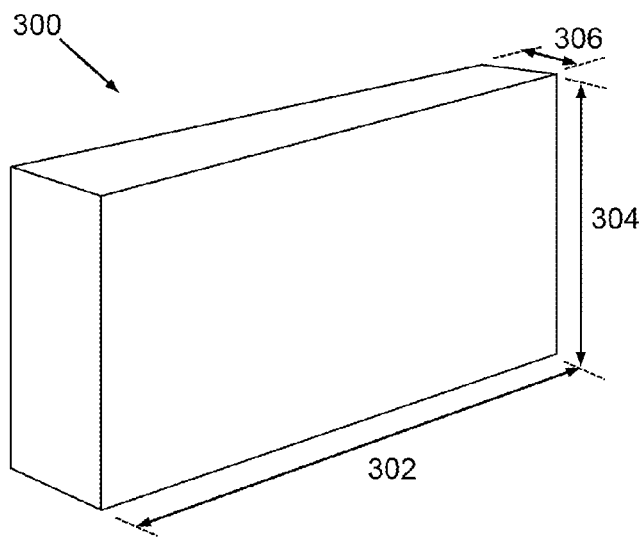
FIG. 3A is a panel subject to an acoustic load in accordance with a first and second example.

The First example considers a panel subjected to acoustic pressure and corresponds to ESDU 72005 [3]. With reference to FIG. 3A, the dimensions of panel 300 are:

Length 302=210 mm
Width 304=140 mm
Thickness 306=1.2 mm

The panel material is an aluminium alloy with Young's modulus E=70 GPa and density $\rho$=2770 kg/m$^3$. The panel critical modal damping ratio is $\zeta$=0.017.

Consistent with ESDU 72005 the pressure spectrum level, $L_{ps}$, is 124 dB and is applied uniformly over a frequency range of 0 Hz to 2200 Hz. Using Equations 3 and 4, the RMS pressure, $p_{rms}$, is 31.62 MPa and the power spectral density, $G(\omega)$, is 1000 (Pa/Hz)$^2$.

In the present example, the panel is discretised using 42 elements along the long side and 28 elements along the short side to produce a mesh with 1176 elements.

The first 20 modes are determined using the NASTRAN™ SOL 103 solver (FEM modal analysis) and the NASTRAN™ bulk data card "EIGRL" for real eigenvalue analysis using the Lanczos algorithm for finding eigenvalues and eigenvectors or a square matrix. It will be appreciated to those skilled in the art that any suitable solution algorithm may be employed to determine the eigenvalues and eigenvectors.

The output of this analysis for the first four modes is provided in Table 1 below.

TABLE 1

NASTRAN™ Modal Analysis (Modes 1-4; mass normalised)

| Mode | Frequency (Hz) | Max Disp. (m) | Layer | Stress XX (Pa) | Stress YY (Pa) | Stress XY (Pa) |
|---|---|---|---|---|---|---|
| 1 | 404.43 | −7.938 | Top | −1.523E+11 | −5.118E+11 | −8.721E+08 |
|   |        |        | Bottom | 1.523E+11 | 5.118E+11 | 8.721E+08 |
| 2 | 623.15 | 7.577 | Top | −1.414E+10 | −4.854E+10 | 3.737E+10 |
|   |        |       | Bottom | 1.414E+10 | 4.854E+10 | −3.737E+10 |
| 3 | 989.63 | 7.359 | Top | −3.699E+11 | −1.241E+12 | −1.774E+09 |
|   |        |       | Bottom | 3.699E+11 | 1.241E+12 | 1.774E+09 |
| 4 | 993.09 | −7.430 | Top | 1.668E+11 | 5.923E+11 | 7.660E+09 |
|   |        |        | Bottom | −1.668E+11 | −5.923E+11 | −7.660E+09 |

The maximum modal displacement is determined from Table 1 and the characteristic modal pressure for the maximum modal displacement is calculated using Equation 7. The output of this analysis for the first four modes is provided in Table 2 below.

TABLE 2

Modal Characteristic Pressure (Modes 1-4; mass normalised)

| Mode | Frequency (Hz) | Max Disp. (m) | Characteristic Pressure $\bar{P}_i$ (MPa) |
|---|---|---|---|
| 1 | 404.43 | −7.938 | 1.70E+02 |
| 2 | 623.15 | 7.577 | 3.86E+02 |
| 3 | 989.63 | 7.359 | 9.46E+02 |
| 4 | 993.09 | −7.430 | 9.62E+02 |

The intermediate RMS stresses are calculated using the Miles equation term for random loading as shown in Equation 6. For pure bending, only the magnitude is considered. The output of this analysis for the first four modes is provided in Table 3 below.

TABLE 3

Modal Bending Stresses (Modes 1-4; mass normalised)

| Mode | Frequency (Hz) | Characteristic Pressure (MPa) | Bending Stress XX (MPa) | Bending Stress YY (MPa) | Bending Stress XY (MPa) |
|---|---|---|---|---|---|
| 1 | 404.43 | 1.70E+02 | 1.523E+05 | 5.118E+05 | 8.721E+02 |
| 2 | 623.15 | 3.86E+02 | 1.414E+04 | 4.854E+04 | 3.737E+04 |
| 3 | 989.63 | 9.46E+02 | 3.699E+05 | 1.241E+06 | 1.774E+03 |
| 4 | 993.09 | 9.62E+02 | 1.668E+05 | 5.923E+05 | 7.660E+03 |

The modal correction factors (joint acceptance factors) are calculated from Equations 15 and 16. The principal acoustic RMS stresses are calculated from Equation 8 and shown in Table 4 below.

TABLE 4

Principal Stresses (Modes 1-4; mass normalised)

| Mode | Frequency (Hz) | $J_{rr}$ | $s_{rms}XX$ (MPa) | $s_{rms}YY$ (MPa) | $s_{rms}XY$ (MPa) | Principal Stress (MPa) |
|---|---|---|---|---|---|---|
| 1 | 404.43 | 1.718 | 6.655 | 22.363 | 0.038 | 22.363 |
| 2 | 623.15 | 0.000 | 0.000 | 0.000 | 0.000 | 0.000 |

TABLE 4-continued

Principal Stresses (Modes 1-4; mass normalised)

| Mode | Frequency (Hz) | $J_{rr}$ | $s_{rms}XX$ (MPa) | $s_{rms}YY$ (MPa) | $s_{rms}XY$ (MPa) | Principal Stress (MPa) |
|---|---|---|---|---|---|---|
| 3 | 989.63 | 0.000 | 0.000 | 0.000 | 0.000 | 0.000 |
| 4 | 993.09 | 0.665 | 0.783 | 2.781 | 0.036 | 2.782 |

The corresponding ESDU value of the maximum principle stress is 26.39 MPa [3], which compares favourably with the modelled value of 22.363 MPa as determined according to the present invention. Further refinement of the mesh used can improve the accuracy of the modelled result if required.

Example 2

Curved Panel Subjected to Acoustic Pressure

The second example considers a curved panel subjected to acoustic pressure and corresponds to ESDU 72005 [3]. The panel's nominal dimensions and material properties are the same as those provided above in relation to the first example and FIG. 3A. In the present example, the panel additionally has a radius of curvature, R, of 1.5 m. The properties of the acoustic pressure are also the same as those provided above in relation to the first example.

For the purposes of the NASTRAN™ analysis, an initial coarse mesh of 9 by 7 elements is constructed and the output of the NASTRAN™ modal analysis for the first five modes is provided in Table 5 below.

TABLE 5

NASTRAN™ Modal Analysis (Modes 1-5; mass normalised)

| Mode | Frequency (Hz) | Max Disp. (m) | Layer | Stress XX (Pa) | Stress YY (Pa) | Stress XY (Pa) |
|---|---|---|---|---|---|---|
| 1 | 607.2 | 7.504 | Top | 1.629E+11 | 1.689E+11 | −4.169E−04 |
|   |       |       | Bottom | −5.882E+11 | −2.813E+11 | 2.803E−04 |
| 2 | 759.6 | 6.932 | Top | −5.481E−03 | −5.474E−03 | −4.683E−04 |
|   |       |       | Bottom | 2.023E−02 | 9.355E−03 | 1.548E−02 |
| 3 | 988.1 | 7.169 | Top | −2.076E−02 | −7.766E−03 | 7.583E−03 |
|   |       |       | Bottom | −3.640E−02 | −6.311E−03 | −5.514E−03 |
| 4 | 1077.4 | 7.169 | Top | 2.519E+11 | 8.893E+11 | 6.502E−03 |
|   |       |       | Bottom | −6.755E+11 | −9.472E+11 | −4.275E−03 |
| 5 | 1181.3 | 6.781 | Top | −8.405E−04 | −9.109E−03 | 4.697E+11 |
|   |       |       | Bottom | 3.040E−03 | 8.823E−03 | −3.040E+11 |

The magnitude of the bending stress, $\sigma_{bending}$, in each plane is determined from FEM as the difference between the top fibre stress and the bottom fibre stress divided by two (assuming uniform thickness of the panel): $\sigma_{bending} = |\sigma_{top} - \sigma_{bottom}|/2$. Table 6 shows the bending stresses calculated for the present example.

TABLE 6

Modal Bending Stresses (Modes 1-5; mass normalised)

| Mode | Frequency (Hz) | Characteristic Pressure (Pa) | Bending stress XX (Pa) | Bending stress YY (Pa) | Bending stress XY (Pa) |
|---|---|---|---|---|---|
| 1 | 607.2 | 3.72E+08 | 3.755E+11 | 2.251E+11 | 3.486E−04 |
| 2 | 759.6 | 5.23E+08 | 1.285E−02 | 7.414E−03 | 7.973E−03 |
| 3 | 988.1 | 1.05E+09 | 7.822E−03 | 7.276E−04 | 6.548E−03 |
| 4 | 1077.4 | 1.22E+09 | 4.637E+11 | 9.182E+11 | 5.389E−03 |
| 5 | 1181.3 | 1.54E+09 | 1.940E−03 | 8.966E−03 | 3.869E+11 |

Next, the modal correction factors (i.e. the joint acceptance factors) are calculated and the overall RMS principle (bending) stresses for each mode of interest are calculated from Equations 15 and 16, as shown Table 7.

TABLE 7

RMS Principal Stresses (Modes 1-5; mass normalised)

| Mode | Frequency (Hz) | Jrr | $s_{rms}$ XX (MPa) | $s_{rms}$ YY (MPa) | $s_{rms}$ XY (MPa) | Principal Stress (MPa) |
|---|---|---|---|---|---|---|
| 1 | 607.2 | 2.462 | 12.917 | 7.742 | 0.000 | 12.92 |
| 2 | 759.6 | 1.333 | 0.000 | 0.000 | 0.000 | 0.00 |
| 3 | 988.1 | 1.458 | 0.000 | 0.000 | 0.000 | 0.00 |
| 4 | 1077.4 | 0.951 | 1.513 | 5.342 | 0.000 | 5.34 |
| 5 | 1181.3 | 0.000 | 0.000 | 0.000 | 0.000 | 0.00 |

From Table 7, it will be evident that the RMS principal stress in the first mode is approximately 12.92 MPa. Further refining of the mesh to 42 by 28 elements results in a RMS principal stress of approximated to 14.02 MPa for the curved panel. This compares favourably with the value of 15.30 MPa obtained from the EDSU data set [3].

Example 3

Bracket Subjected to Random Inertial Loading

Figure 3B:
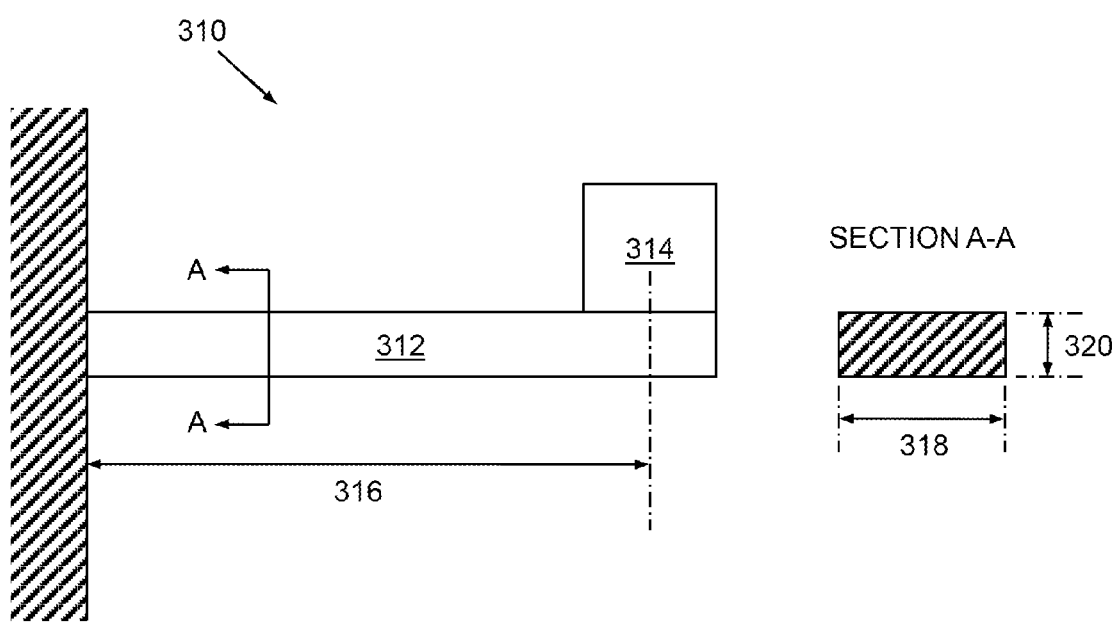
FIG. 3B is a cantilevered bracket subject to a random load in accordance with a third example.

A third example, based on an example in [5], is provided to demonstrate application of embodiments of the present invention where the random loading is induced by inertial effects. FIG. 3B shows the example 310 comprising cantilevered bracket 312 with a system mass 314 mounted at the free end of the bracket. With reference to FIG. 3B, the dimensions of the bracket 312 are:

Length 316, l: =6 inch (15.24 mm)
Width 318, w: =0.5 inch (12.7 mm)
Thickness 320, t: =0.3 inch (7.62 mm).

The panel material is an aluminium alloy with Young's modulus E=70 GPa and density ρ=2770 kg/m³. The critical modal damping ratio of the bracket is ζ=0.033. The mass of the bracket is ρwtl=0.03982 kg and the bracket system mass 314, M, is 0.227 kg. Thus, the total mass, m, of the system is (M+ρAl)=0.26682 kg. The bracket 312 is subject to a white noise vibration $G_{PSD}$ of 0.3 g²/Hz.

A FEM modal analysis is performed using the NASTRAN™ SOL 103 solver to determine deflections for each mode. The characteristic pressure for each mode, i, can be related to the deflection according to $$\bar{P}_i = m(2\pi\omega_i)^2 |\phi_i(x,y,z)| = (M+\rho Al)(2\pi\omega_i)^2 |\phi_i(x,y,z)|. \quad (17)$$

The results of the modal analysis of and characteristic forces for each mode are provided in Table 8.

TABLE 8

Characteristic Force (Modes 1-5; mass normalised)

| Mode | Frequency (Hz) | Max Disp. (m) | Max Stress (Node 1) $\square_{max}$ (MPa) | Characteristic Force (N) |
|---|---|---|---|---|
| 1 | 54.57 | 2.058 | 1.19E+11 | 6.45E+04 |
| 2 | 90.96 | 2.058 | 7.14E+10 | 1.79E+05 |
| 3 | 1195.34 | 7.493 | 2.98E+12 | 1.13E+08 |
| 4 | 1992.24 | 7.493 | 1.79E+12 | 3.13E+08 |
| 5 | 2165.24 | 2.040 | 9.63E+11 | 1.01E+08 |

The Miles equation for random process of Equation 6 is applied to calculate the intermediate stresses and deformations of the cantilever bracket. Next, the modal correction factors (or the joint acceptance factors) are calculated from Equations 15 and 16 and are used to calculate the overall RMS stresses according to Equation 8. The results of this analysis are provided in Table 9.

TABLE 9

Maximum RMS Stress at Node 1 (Modes 1-5; mass normalised)

| Mode | Frequency (Hz) | Jrr | Max RMS stress $\square_{rms}$ (MPa) | Principal Stress (MPa) |
|---|---|---|---|---|
| 1 | 54.57 | 1.513 | 36.404 | 55.07 |
| 2 | 90.96 | 1.513 | 10.151 | 15.36 |

TABLE 9-continued

Maximum RMS Stress at Node 1 (Modes 1-5; mass normalised)

| Mode | Frequency (Hz) | Jrr | Max RMS stress $\square_{rms}$ (MPa) | Principal Stress (MPa) |
|---|---|---|---|---|
| 3 | 1195.34 | 1.285 | 2.444 | 3.14 |
| 4 | 1992.24 | 1.285 | 0.682 | 0.88 |
| 5 | 2165.24 | 1.441 | 1.190 | 1.72 |

It will be apparent from Table 9 that the maximum RMS stress is 55.07 MPa, corresponding to the first mode of vibration. This value compares favourably with a maximum RMS stress value of 54.4 MPa obtained from a full random power spectrum density analysis using FEM.

The above embodiments are to be understood as illustrative examples of the invention and further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

REFERENCES

1. Blevins R. D., "An Approximate Method for Sonic Fatigue Analysis of Plates and Shells", Journal of Sound and Vibration, 129(1), 1989, pp 51-71.
2. Bathe K. J., "Finite Element Procedures", Prentice-Hall International, inc., 1996.
3. ESDU Vibration and Acoustic series, HIS ESDU, London, United Kingdom.
4. John W. Miles, On Structural Fatigue Under Random Loading, Journal of the Aeronautical Sciences, pg. 753, November, 1954.
5. Steinberg D., "Vibration Analysis for Electronic Equipment", 3rd edition, John Wiley and Sons Inc., 2000.

The invention claimed is:

1. A computer-implemented method of modelling a root-mean-square stress in a structure induced by a random load applied to the structure, the method comprising:
storing, in a non-transitory memory of an analysis engine, data representing an eigensolution of the structure in free vibration in a first mode of vibration;
storing in the non-transitory memory, data representing a modal stress in the structure induced by the free vibration in the first mode of vibration;
determining, by a processor of the analysis engine, a modal correction factor which characterizes a proportion of the random load contributing to a response of the structure in the first mode of vibration, wherein the determination of the modal correction factor includes the processor accessing the stored data representing the eigensolution of the structure in the first mode of vibration and analyzing the data to determine the modal correction factor;
generating, by the processor, data representing a stress in the structure induced by a forced vibration in the first mode of vibration, based on the data representing the modal stress in the structure induced by the free vibration in the first mode of vibration;
generating, by the processor, data representing a root-mean-square stress in the structure induced by the random load by applying the modal correction factor to the data representing the stress in the structure induced by the forced vibration in the first mode of vibration;
applying the data representing the root-mean-square stress to determine a strength or fatigue endurance of the structure, and
determining whether the structure is worthy for service based on the strength or fatigue endurance of the structure.

2. The computer-implemented method of modelling a root-mean-square stress in a structure according to claim 1, wherein the method further comprises generating the data representing the eigensolution of the structure using a finite element method modal analysis.

3. The computer-implemented method of modelling a root-mean-square stress in a structure according to claim 1, wherein the random load is characterised by a power spectral density.

4. The computer-implemented method of modelling a root-mean-square stress in a structure according to claim 1, wherein, for a particular location in the structure, the stress due to the forced vibration is determined as being proportional to a corresponding modal stress in the structure in free vibration.

5. The computer-implemented method of modelling a root-mean-square stress in a structure according to claim 4, wherein, for a particular location in the structure, the ratio of the stress in the structure due to the forced vibration and the modal stress in the structure due to the free vibration is determined using the Miles equation:

$$\frac{\sigma_i(x, y, z)_{rms}}{\overline{\sigma}_i(x, y, z)} = \sqrt{\frac{\pi \omega_i}{4\zeta_i} \frac{G(\omega_i)}{\overline{P}_i^2}},$$

where $\sigma_i(x,y,z)_{rms}$ is the stress at a position x, y, z in the structure due to the forced vibration; $\overline{\sigma}_i(x,y,z)$ is the modal stress at a position x, y, z in due to free vibration in mode i; $\omega_i$ is the frequency of mode i; $\zeta_i$ is the critical damping for mode i; $G(\omega_i)$ is the power spectral density characterising the random load; and $\overline{P}_i$ is a characteristic pressure for mode i.

6. A computer-implemented method of modelling a root-mean-square stress in a structure, induced by a random load applied to the structure, the method comprising:
storing, in a non-transitory memory of an analysis engine, data representing an eigensolution of the structure in free vibration in a first mode of vibration;
storing in the non-transitory memory, data representing a modal stress in the structure induced by the free vibration in the first mode of vibration;
determining, by a processor of the analysis engine, a modal correction factor which characterizes a proportion of the random load contributing to a response of the structure in the first mode of vibration, wherein the determination of the modal correction factor includes the processor accessing the stored data representing the eigensolution of the structure in the first mode of vibration and analyzing the data to determine the modal correction factor, wherein the modal correction factor is calculated as:

$$J_i = \frac{[\phi]_i^T \begin{Bmatrix} 1 \\ \vdots \\ 1 \end{Bmatrix}}{[\phi]_i^T [\phi]_i},$$

where: $J_i$ is the modal correction factor for mode i; and $[\phi]_i$ is the eigenvector solution for mode [I]i;

generating, by the processor, data representing a stress in the structure induced by a forced vibration in the first mode of vibration, based on the data representing the modal stress in the structure induced by the free vibration in the first mode of vibration;

generating, by the processor, data representing a root-mean-square stress in the structure induced by the random load by applying the modal correction factor to the data representing the stress in the structure induced by the forced vibration in the first mode of vibration;

applying the data representing the root-mean-square stress to determine a strength or fatigue endurance of the structure, and determining whether the structure is worthy for service based on the determined strength or fatigue endurance of the structure.

7. The computer-implemented method of modelling a root-mean-square stress in a structure according to claim 1, further comprising displaying, using a visual display device, the root-mean-square stresses determined for a plurality of locations in the structure for inspection by a user.

8. The computer-implemented method of modelling a root-mean-square stress in a structure according to claim 1, wherein the random load is an acoustic pressure.

9. A computer-implemented method of modelling a root-mean-square stress in a structure, in a structure induced by an acoustic pressure applied to the structure, the method comprising storing, in a non-transitory memory of an analysis engine, data representing an eigensolution of the structure in free vibration in a first mode of vibration;

storing in the non-transitory memory, data representing a modal stress in the structure induced by the free vibration in the first mode of vibration;

determining, by a processor of the analysis engine, a modal correction factor which characterizes a proportion of the acoustic pressure contributing to a response of the structure in the first mode of vibration, wherein the determination of the modal correction factor includes the processor accessing the stored data representing the eigensolution of the structure in the first mode of vibration and analyzing the data to determine the modal correction factor;

generating, by the processor, data representing a stress in the structure induced by a forced vibration in the first mode of vibration, based on the data representing the modal stress in the structure induced by the free vibration in the first mode of vibration;

generating, by the processor, data representing a root-mean-square stress in the structure induced by the acoustic pressure by applying the modal correction factor to the data representing the stress in the structure induced by the forced vibration in the first mode of vibration;

applying the data representing the root-mean-square stress to determine a strength or fatigue endurance of the structure, and determining whether the structure is worthy for service based on the strength or fatigue endurance of the structure;

wherein the acoustic pressure is characterised as:

$$p_{rms} = 10^{\left[\frac{L_{ps}}{20} - 4.69897\right]},$$

where $p_{rms}$ is the root-mean-square pressure and $L_{ps}$ is the sound pressure spectrum level.

10. A computer program product comprising a non-transitory computer-readable storage medium having computer readable instructions stored thereon, the computer readable instructions being executable by a computerised device to cause the computerised device to perform a method of modelling a root-mean-square stress in a structure induced by a random load, the method comprising:

storing, in the non-transitory computer readable storage medium, data representing an eigensolution of the structure in free vibration in a first mode of vibration;

storing in the non-transitory computer readable storage medium, data representing a modal stress in the structure induced by the free vibration in the first mode of vibration;

determining a modal correction factor which characterizes a proportion of the random load contributing to a response of the structure in the first mode of vibration, wherein the determination of the modal correction factor includes accessing the stored data representing the eigensolution of the structure in the first mode of vibration and analyzing the data to determine the modal correction factor;

generating data representing a stress in the structure induced by a forced vibration in the first mode of vibration, wherein the data is generated based on the data representing the modal stress in the structure induced by free vibration in the first mode of vibration;

generating data representing a root-mean-square stress in the structure induced by the random load by applying the modal correction factor to the data representing the stress in the structure induced by the forced vibration in the first mode of vibration;

applying the data representing the root-mean-square stress to determine a strength or fatigue endurance of the structure, and determining whether the structure is worthy for service based on the strength or fatigue endurance of the structure.

11. The computer program product according to claim 10, wherein the method further comprises determining the eigensolution using a finite element method modal analysis.

12. The computer program product according to claim 10, wherein the random load is characterised by a power spectral density.

13. The computer program product according to claim 10, wherein, for a particular location in the structure, the stress due to the forced vibration is determined as being proportional to a corresponding modal stress in free vibration.

14. The computer program product according to claim 13, wherein, for a particular location in the structure, the ratio of the stress in the structure due to the forced vibration and the modal stress in the structure due to the free vibration is determined using the Miles equation:

$$\frac{\sigma_i(x, y, z)_{rms}}{\overline{\sigma}_i(x, y, z)} = \sqrt{\frac{\pi \omega_i}{4 \zeta_i} \frac{G(\omega_i)}{\overline{P}_i^2}},$$

where $\sigma_i(x,y,z)_{rms}$ is the stress at a position x, y, z in the structure due to the forced vibration; $\overline{\sigma}_i(x,y,z)$ is the modal stress at a position x, y, z in due to free vibration in mode i; $\omega_i$ is the frequency of mode i; $\zeta_i$ is the critical damping for mode i; $G(\omega_i)$ is the power spectral density characterising the random load; and $\overline{P}_i$ is a characteristic pressure for mode i.

15. A computer program product, comprising a non-transitory computer-readable storage medium having computer readable instructions stored thereon, the computer readable instructions being executable by a computerised device to cause the computerised device to perform a method of modelling a root-mean-square stress in a structure induced by a random load, the method comprising:
   storing, in the non-transitory computer readable storage medium, data representing an eigensolution of the structure in free vibration in a first mode of vibration;
   storing in the non-transitory computer readable storage medium, data representing a modal stress in the structure induced by the free vibration in the first mode of vibration; determining a modal correction factor which characterizes a proportion of the random load contributing to a response of the structure in the first mode of vibration, wherein the determination of the modal correction factor includes accessing the stored data representing the eigensolution of the structure in the first mode of vibration and analyzing the data to determine the modal correction factor, wherein the modal correction factor is calculated as:

$$J_i = \frac{[\phi]_i^T \begin{Bmatrix} 1 \\ \vdots \\ 1 \end{Bmatrix}}{[\phi]_i^T [\phi]_i},$$

where: $J_i$ is the modal correction factor for mode i; and $[\phi]_i$ is the eigenvector solution for mode i;
   generating data representing a stress in the structure induced by a forced vibration in the first mode of vibration, wherein the data is generated based on the data representing the modal stress in the structure induced by free vibration in the first mode of vibration;
   generating data representing a root-mean-square stress in the structure induced by the random load by applying the modal correction factor to the data representing the stress in the structure induced by the forced vibration in the first mode of vibration;
   applying the data representing the root-mean-square stress to determine a strength or fatigue endurance of the structure, and
   determining whether the structure is worthy for service based on the determined strength or fatigue endurance of the structure.

16. The computer program product according to claim 10, further comprising displaying, using a visual display device, the root-mean-square stresses determined for a plurality of locations in the structure for inspection by a user.

17. The computer program product according to claim 10, wherein the random load is an acoustic pressure.

18. A computer program product, comprising a non-transitory computer-readable storage medium having computer readable instructions stored thereon, the computer readable instructions being executable by a computerised device to cause the computerised device to perform a method of modelling a root-mean-square stress in a structure induced by an acoustic pressure, the method comprising:
   storing, in the non-transitory computer readable storage medium, data representing an eigensolution of the structure in free vibration in a first mode of vibration;
   storing in the non-transitory computer readable storage medium, data representing a modal stress in the structure induced by the free vibration in the first mode of vibration;
   determining a modal correction factor which characterizes a proportion of the acoustic pressure contributing to a response of the structure in the first mode of vibration, wherein the determination of the modal correction factor includes accessing the stored data representing the eigensolution of the structure in the first mode of vibration and analyzing the data to determine the modal correction factor;
   generating data representing a stress in the structure induced by a forced vibration in the first mode of vibration, wherein the data is generated based on the data representing the modal stress in the structure induced by free vibration in the first mode of vibration;
   generating data representing a root-mean-square stress in the structure induced by the acoustic pressure by applying the modal correction factor to the data representing the stress in the structure induced by the forced vibration in the first mode of vibration;
   applying the data representing the root-mean-square stress to determine a strength or fatigue endurance of the structure, and
   determining whether the structure is worthy for service based on the strength or fatigue endurance of the structure;
   wherein the acoustic pressure is characterised as:

$$p_{rms} = 10^{\left[\frac{L_{ps}}{20} - 4.69897\right]},$$

where $p_{rms}$ is the root-mean-square pressure and $L_{ps}$ is the sound pressure spectrum level.

19. A computer apparatus for modelling a root-mean-square stress in a structure induced by a random load, the apparatus comprising a processor and a non-transitory memory configured to:
   store in the non-transitory memory data representing an eigensolution of the structure in free vibration in a first mode of vibration;
   store in the non-transitory memory, data representing a modal stress in the structure induced by the free vibration in the first mode of vibration;
   determine, by the processor, a modal correction factor that characterizes a proportion of the random load contributing to a response of the structure in the first mode of vibration, wherein the determination of the modal correction factor includes the processor accessing the stored data representing the eigensolution of the structure in the free vibration in the first mode of vibration and analysing the data to determine the modal correction factor; and generate, by the processor, data representing a stress in the structure induced by the forced vibration in the first mode of vibration, wherein the data is generated based on the data representing the modal stress in the structure induced by the free vibration in the first mode of vibration;

generate, by the processor, data representing a root-mean-square stress in the structure induced by the random load by applying the modal correction factor to the data representing the stress in the structure induced by the forced vibration in the first mode of vibration;

apply the data representing the root-mean-square stress to determine a strength or fatigue endurance of the structure, and determine whether the structure is worthy for service based on the strength or fatigue endurance of the structure.

* * * * *